(12) United States Patent
Wolf et al.

(10) Patent No.: US 9,308,287 B2
(45) Date of Patent: Apr. 12, 2016

(54) FRAGRANCING SYSTEM FOR A MOTOR VEHICLE

(71) Applicant: MAHLE INTERNATIONAL GmbH, Stuttgart (DE)

(72) Inventors: Walter Wolf, Oppenweiler-Zell (DE); Eric Pitz, Stuttgart (DE); Tobias Baumann, Bietigheim-Bissingen (DE)

(73) Assignee: MAHLE INTERNATONAL GmbH, Stuttgart (DE)

( * ) Notice: Subject to any disclaimer, the term of this patent is extended or adjusted under 35 U.S.C. 154(b) by 0 days.

(21) Appl. No.: 14/549,090

(22) Filed: Nov. 20, 2014

(65) Prior Publication Data
US 2015/0137395 A1 May 21, 2015

(30) Foreign Application Priority Data

Nov. 20, 2013 (DE) .......................... 10 2013 223 738

(51) Int. Cl.
*A61L 9/12* (2006.01)
*B60H 3/00* (2006.01)

(52) U.S. Cl.
CPC . *A61L 9/122* (2013.01); *A61L 9/12* (2013.01); *B60H 3/0007* (2013.01); *B60H 2003/0057* (2013.01)

(58) Field of Classification Search
CPC ....... A61L 9/12; A61L 9/122; B01F 3/04099; B01F 2003/04872; B01F 2003/04943; B01F 2215/009; B60H 3/0007; B60H 2003/0057
USPC ....................... 261/30, 142, DIG. 88, DIG. 89
See application file for complete search history.

(56) References Cited

U.S. PATENT DOCUMENTS

| 4,903,584 | A * | 2/1990 | Styles ....................... A61L 9/12 239/57 |
| 6,592,828 | B2 | 7/2003 | Quintana Munoz |
| 6,852,278 | B2 * | 2/2005 | Richards ............. A01M 1/2055 239/58 |
| 8,544,766 | B2 * | 10/2013 | Webster .................... A61L 9/12 239/34 |
| 2004/0077424 | A1 | 4/2004 | Murphy et al. |
| 2008/0257915 | A1 * | 10/2008 | Wold .................... B05B 11/025 222/389 |
| 2010/0140298 | A1 * | 6/2010 | Anderson ................. A61L 9/12 222/183 |
| 2013/0277456 | A1 * | 10/2013 | Fehling .................... A61L 9/12 239/302 |
| 2014/0041524 | A1 * | 2/2014 | Talbot ...................... A61L 9/03 96/222 |
| 2014/0367408 | A1 * | 12/2014 | D'Amico ............... A61L 9/012 222/1 |

FOREIGN PATENT DOCUMENTS

| DE | 197 15 404 A1 | 2/1998 |
| DE | 102 23 344 B4 | 12/2002 |
| DE | 103 05 480 A1 | 8/2004 |
| DE | 103 27 122 A1 | 3/2005 |

(Continued)

*Primary Examiner* — Charles Bushey
*Assistant Examiner* — Scott Bushey
(74) *Attorney, Agent, or Firm* — Muncy, Geissler, Olds & Lowe, P.C.

(57) ABSTRACT

A fragrancing system for a motor vehicle, having a housing, in which a replaceable fragrance storage container is inserted, which has an opening for dispensing a fragrance which is covered by a closure mechanism which frees the opening for dispensing of the fragrance when actuated by an actuator. In a fragrancing system which is of simple construction and nevertheless operates reliably, the housing is provided with a cover, which for introduction of the fragrance storage container is mounted so as to be pivotable about an axis of rotation into a housing interior, wherein when the fragrance storage container is introduced it is locked by the cover.

10 Claims, 10 Drawing Sheets

(56) References Cited

FOREIGN PATENT DOCUMENTS

| DE | 602 04 467 T2 | 2/2006 |
| DE | 10 2007 038 222 A1 | 2/2009 |
| DE | 10 2008 033 884 A1 | 2/2009 |
| DE | 10 2008 007 075 A1 | 8/2009 |
| DE | 10 2008 032 612 A1 | 1/2010 |
| DE | 10 2008 032 613 A1 | 1/2010 |
| DE | 10 2008 032 615 A1 | 1/2010 |
| DE | 10 2009 033 020 A1 | 1/2011 |
| DE | 10 2012 224 497 A1 | 7/2014 |

* cited by examiner

FRAGRANCING SYSTEM FOR A MOTOR VEHICLE

This nonprovisional application claims priority to German Patent Application No. DE 10 2013 223 738.3, which was filed in Germany on Nov. 20, 2013, and which is herein incorporated by reference.

BACKGROUND OF THE INVENTION

1. Field of the Invention

The present invention relates to a fragrancing system for a motor vehicle.

2. Description of the Background Art

Nowadays vehicles are increasingly provided with means for improving the air quality. In luxury vehicles ionizers are additionally built into the air ducts for ionization of the air. Fragrance systems can also be positioned at various locations in the motor vehicle.

DE 10 2008 032 613 A1 shows a fragrance storage device which is disposed replaceably in a fragrancing device. The fragrance storage device has a fragrance container unit and a fragrance discharge unit and a coupling unit for coupling to at least one actuator unit. Such a fragrance device is disposed in an air duct in which an air flow generated by a blower flows past the fragrance storage container. By means of an actuator driven by an electric motor the fragrance is released and is transported into the vehicle interior by the air produced by the blower.

A fragrancing system for a motor vehicle which is known from DE 10 2009 033 020 A1 has a fragrance holder unit to hold a liquid fragrance and an air conveyor unit to convey air through the fragrance holder unit, and to introduce fragrance into a vehicle interior by means of the conveyed air, wherein the fragrance holder unit has an inlet opening for introduction of the air conveyed by the air conveyor unit into the fragrance holder unit, and an outlet opening for discharging the conveyed air out of the fragrance holder unit. Such a fragrancing system has a first shut-off device for closing and opening an outlet opening, so that when a first shut-off device is opened fragrance can be introduced into the vehicle interior and when a shut-off device is closed no fragrance can be introduced into the vehicle interior.

According to DE 103 27 122 A1, a ventilating device is disclosed in particular for fragrancing a motor vehicle. This ventilating device comprises a fragrance with a metering device, wherein the fragrancing device has at least one hollow body with at least one opening and comprises an element with at least one further opening, wherein the hollow body and/or the element are driven by means of a motor in such a way that a relative movement between the hollow bodies and the element is possible and in at least one position of the relative movement the two openings facilitate a passage of the fragrance from the interior outwards.

DE 103 05 480 A1 shows a fragrance dispenser for the interior of a vehicle, which dispenser comprises a container with fragrance which is connected to a heating element and a connector for connection to a cigarette lighter of the motor vehicle. As soon as the vehicle is started, by means of the cigarette lighter the heating element is activated and as a result so is the fragrance dispenser.

A refillable electric air freshener for automobiles is shown in DE 102 23 344 B4, which corresponds to U.S. Pat. No. 6,592,828. The air freshener can be connected to a voltage source, wherein the voltage source takes the form of the cigarette lighter of the vehicle. The air freshener comprises a housing in which an electrical circuit having two connecting terminals is formed and an accommodating space is provided in which an air freshening substance is accommodated and protected, wherein the housing has openings for the substance to flow out and on the housing at least one laterally disposed retaining spring is provided which at the same time is formed as one of the connecting terminals of the circuit. In the circuit a manually actuated electrical switch is provided which has two switching positions for closing and opening the circuit in order thus to facilitate the dispensing of the fragrance from the substance.

The described fragrancing systems are very complex in design and are designed being for a fixed location in the motor vehicle.

SUMMARY OF THE INVENTION

It is therefore an object of the present invention to provide a fragrancing system for a motor vehicle which is simple to produce and can be installed at any required location on the motor vehicle.

An embodiment of the invention relates to a fragrancing system with a housing provided with a cover which is mounted so as to be rotatable about an axis of rotation into the interior of the housing for introduction of the fragrance, wherein when the fragrance storage container is introduced it is locked by the cover. Because of the mobile construction of the housing with the fragrance storage container contained replaceably therein, such a fragrancing system can be retrofitted simply and placed flexibly in a motor vehicle. It may simply be inserted into a cup holder of the motor vehicle. However it is also conceivable that it can be used with a suction foot for fastening to a window pane or other vehicle interior, since it is not bound to a specific fastening site.

The locking of the fragrance storage container can take place via a projection which is formed on the fragrance storage container or a recess which is formed on the fragrance storage container and in which the cover pivoted into the housing interior engages. Because of the minimum number of components necessary for the locking only a small installation space is required, so that the fragrancing system can be configured to be very easy to handle.

In an embodiment an ejector spring pretensioned against the fragrance storage container is formed below the fragrance storage container on the housing, wherein in the event of a movement of the fragrance storage container beyond the lock in the direction of the ejector spring the cover forming the lock is movable laterally so that the fragrance storage container can be led out of the housing. When the fragrance storage container is replaced the cover remains in the housing. Thus a simple and also very quick change of the fragrance storage container is possible.

In a variant, the closure mechanism of the opening of the fragrance storage container can be constructed as a pivotable flap in the housing interior, wherein the flap which is rotatably mounted close to an opening in the housing and projects beyond the longitudinal extent of the fragrance storage container in the housing interior is pivotable out of a rest position closing the opening by the linear actuator disposed below the fragrance storage container and acting on a freely movable flap overlap, wherein a rotatable bearing and the flap overlap are constructed at opposite ends of the flap. The fragrancing system has only a few movable parts, so that a susceptibility to malfunction of the fragrancing system upon actuation thereof is limited. Furthermore a fail-safe function is provided, since the fragrance storage container is always closed when the actuator is not active and thus no fragrance can be dispensed into the vehicle.

In an embodiment the linear actuator can be constructed as a solenoid or as a shape memory actuator. Such configuration has the advantage that by comparison with stepping motors or other actuators it is very compact and consumes little energy.

In a modification a restoring spring, which presses the flap against the opening of the fragrance storage container when the linear actuator is inactive, acts on the side of the flap overlap facing away from the linear actuator. Thus the opening of the fragrance storage container is reliably closed at any time when the linear actuator is not supplied with current.

The ejection mechanism can be constructed as a push-push mechanism with a cardioid. Thus the fragrancing system can be operated by means of a simple actuating mechanism. The restoring spring prevents a play from occurring between the actuator and the cover mechanism, in particular in the event of position tolerances of the fragrance storage container in the inserted state in the housing.

In an embodiment, the closure mechanism of the opening of the fragrance storage container can be constructed as a cover of the housing. The number of components of the fragrancing system is further reduced by the use of the closure mechanism as a cover for the housing. Thus furthermore the fragrancing system can be simply cleaned.

A cleaning cartridge can also be inserted in order to clean the cover reliably from inside.

In an embodiment, an air ionizer is disposed in the housing in a first part-channel and the fragrance storage container is disposed in a second part-channel. Thus it is possible to achieve not only improvements in the air quality but simultaneously also cleaning of the air in the vehicle interior.

In an embodiment, a blower for generating a stream of air for transport of the fragrance and/or the ions is constructed below the fragrance storage container and/or below the ionizer. By means of the stream of air generated by the blower the fragrance or the ions from the ionizer are reliably transported to the location where the vehicle occupant requires an improved air situation.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
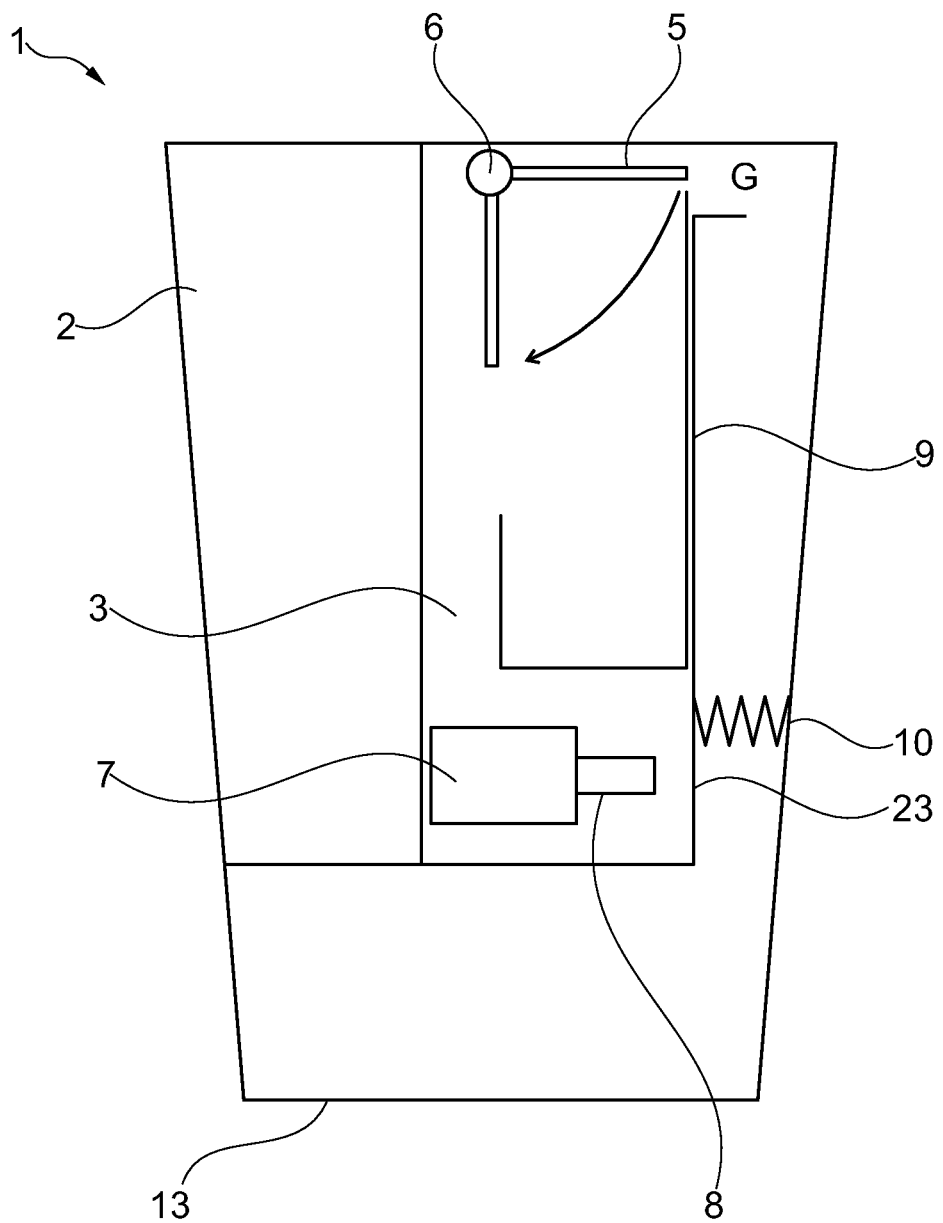
FIG. 1 shows an embodiment of a fragrancing system according to the invention.

FIG. 1 shows a first embodiment of the fragrancing system 1 according to the invention which is configured so as to be mobile and has a housing 2 which has a housing interior 3 in which a fragrance storage container 4 can be positioned. The housing interior 3 is provided with a cover 5 which is fastened to an upper edge of the housing 2 by means of a rotary bearing 6. A drive unit in the form of a linear actuator 7, such as for example a solenoid or a SMA actuator, is disposed close to the base 13 of the housing interior 3 and acts by means of a lever or rod 8 extending parallel to the cover 5 on a closure mechanism 9 constructed as a flap which extends along the housing interior 3 in the direction of the base 13. A restoring spring 10 which is fastened on the housing 2 acts on the side of the closure mechanism 9 opposite the lever 8.

Figure 2:
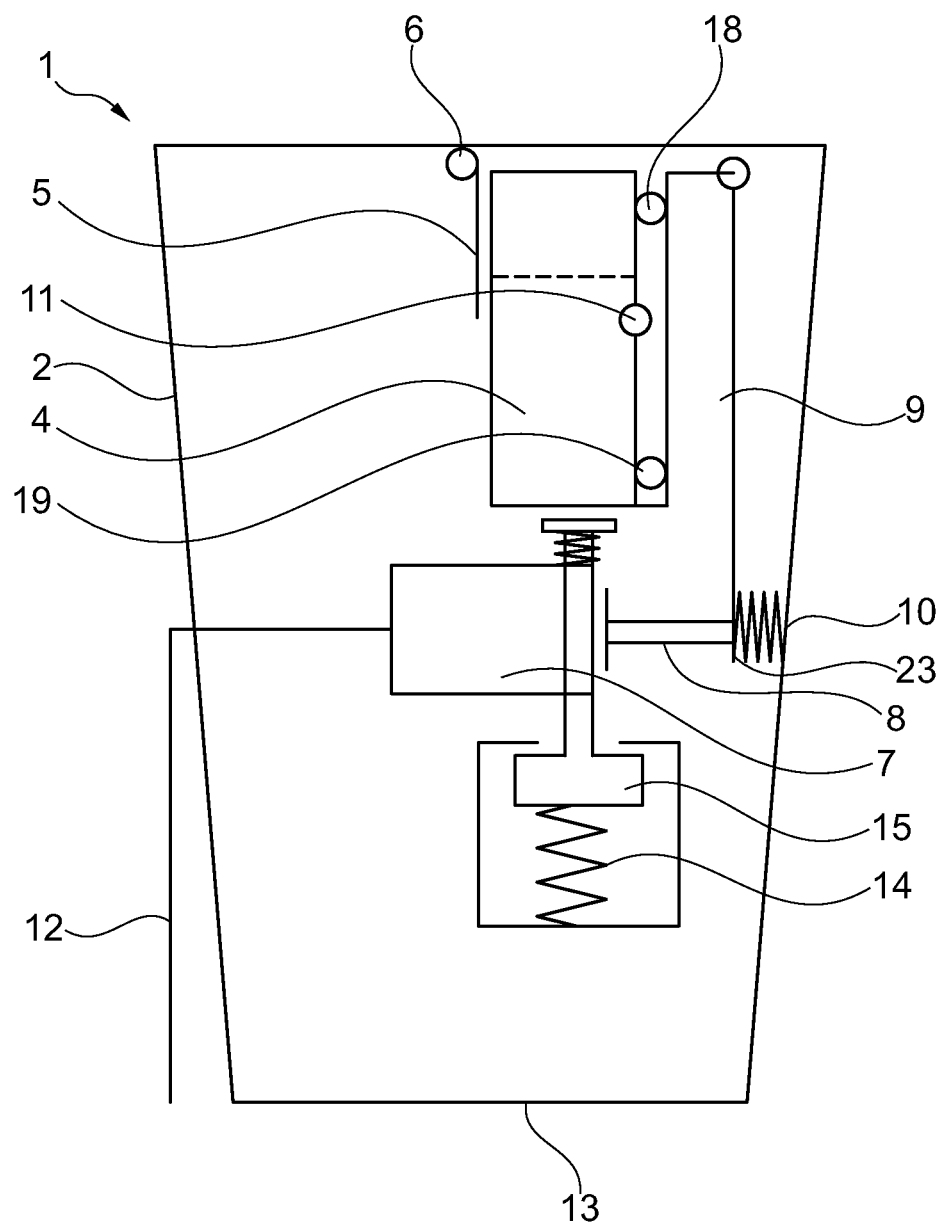
FIG. 2 shows an embodiment of a fragrancing system according to the invention.

As illustrated in FIG. 2, when the fragrance storage container 4 is introduced into the housing interior 3 the cover 5 is moved aside by the fragrance storage container 4, so that the cover 5 protrudes into the housing interior 3. For this purpose one side of the fragrance storage container 4 is oblique in order to facilitate better insertion into the housing 2, so that there is less friction with the seal and the cover 5 can be closed better during the changing operation.

The cover 5 has a four-bar linkage mechanism by which a parallelogram kinematics is produced during changing of the fragrance container. In this case the four-bar linkage mechanism widens the gap between the cover 5 and the fragrance storage container 4.

The fragrance storage container 4 has on its longitudinal extent an opening 11 through which the fragrance is dispensed to the surroundings. In the introduced state of the fragrance storage container 4, this opening 11 is closed by the closure mechanism 9, which is formed as a pivotable flap, provided that the linear actuator 7 is not active. The closure mechanism 9 projects beyond the fragrance storage container 4 in its longitudinal extent and has a flap overlap 23 on which the lever 8 of the linear actuator 7 acts from one side and the restoring spring 10 acts from the other side. When the linear actuator 7 is not activated, the restoring spring 10 presses the closure mechanism 9 against the opening 11 of the fragrance storage container 4. During operation of the linear actuator 7, which is connected by means of an electric line 12 for example to a cigarette lighter or to a USB connector of the motor vehicle, this linear actuator presses by means of the lever 8 against the flap overlap 23, so that the closure mechanism 9 is moved away from the fragrance storage container 4 and the opening 11 is freed. Depending upon the control state of the linear actuator 7, a continuous or a pulsed fragrancing by the fragrance contained in the fragrance storage container 4 is possible. Also a fragrancy intensity setting is adjustable by means of the duration of opening of the opening 11 of the fragrance storage container 4. If no voltage is applied to the linear actuator 7, then the opening 11 of the fragrance storage container 4 is tightly closed by the closure mechanism 9, so that no fragrance discharge is possible.

A further supply of power to the linear actuator 7 can take place by induction, as an inductive current supply is constructed as a separate component in the base 13 of the housing 2 or on the circumference thereof. Alternatively an energy accumulator can also be accommodated in the base region.

Figure 3:
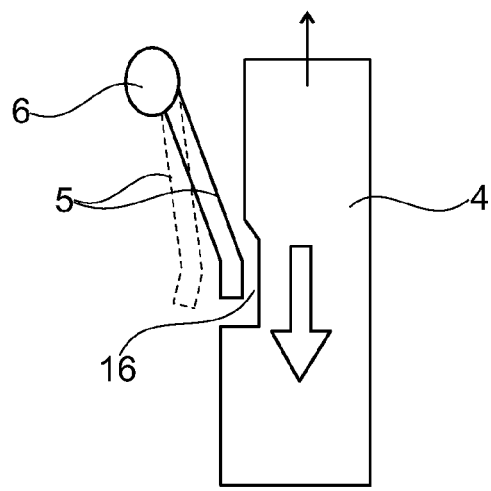
FIG. 3 shows an embodiment of the locking system of the fragrancing system according to the invention.
Figure 4:
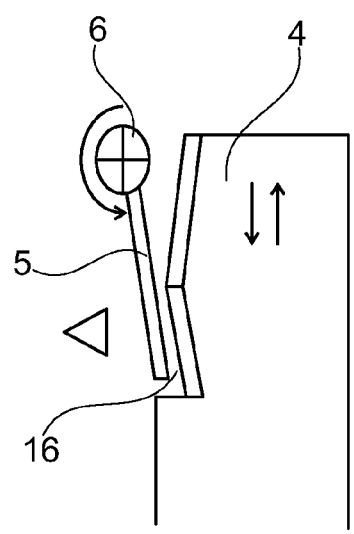
FIG. 4 shows an embodiment of the locking system of the fragrancing system according to the invention.
Figure 5:
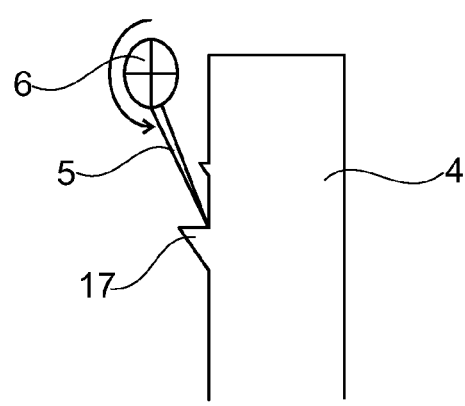
FIG. 5 shows an embodiment of the locking system of the fragrancing system according to the invention.

In the housing interior 3 an ejector spring 14 disposed on the base 13 below the linear actuator 7 bridges the linear actuator 7 and the lever 8 and is pretensioned by means of a plunger 15 against the fragrance storage container 4. When the fragrance storage container 4 is introduced it is locked in the fragrancing system 1 by the tilted cover 5, as this cover 5 presses and engages in a notch 16 on the fragrance storage container 4 (FIG. 3). If the fragrance storage container 4 is empty then, as illustrated in FIG. 4, the fragrance storage container 4 is pressed further in the direction of the base 13, so that the cover 5 slides out of the notch 16 and bears against the inner wall of the housing 2. In this way it is possible that under the pressure of the ejector spring 14 the fragrance storage container 4 can be moved quickly out of the housing 2, removed and replaced. FIG. 5 shows a further possibility for locking the fragrance storage container 4 in the housing 2, wherein a projection 17 on which the cover 5 is supported is disposed on the fragrance storage container 4.

Figure 6:
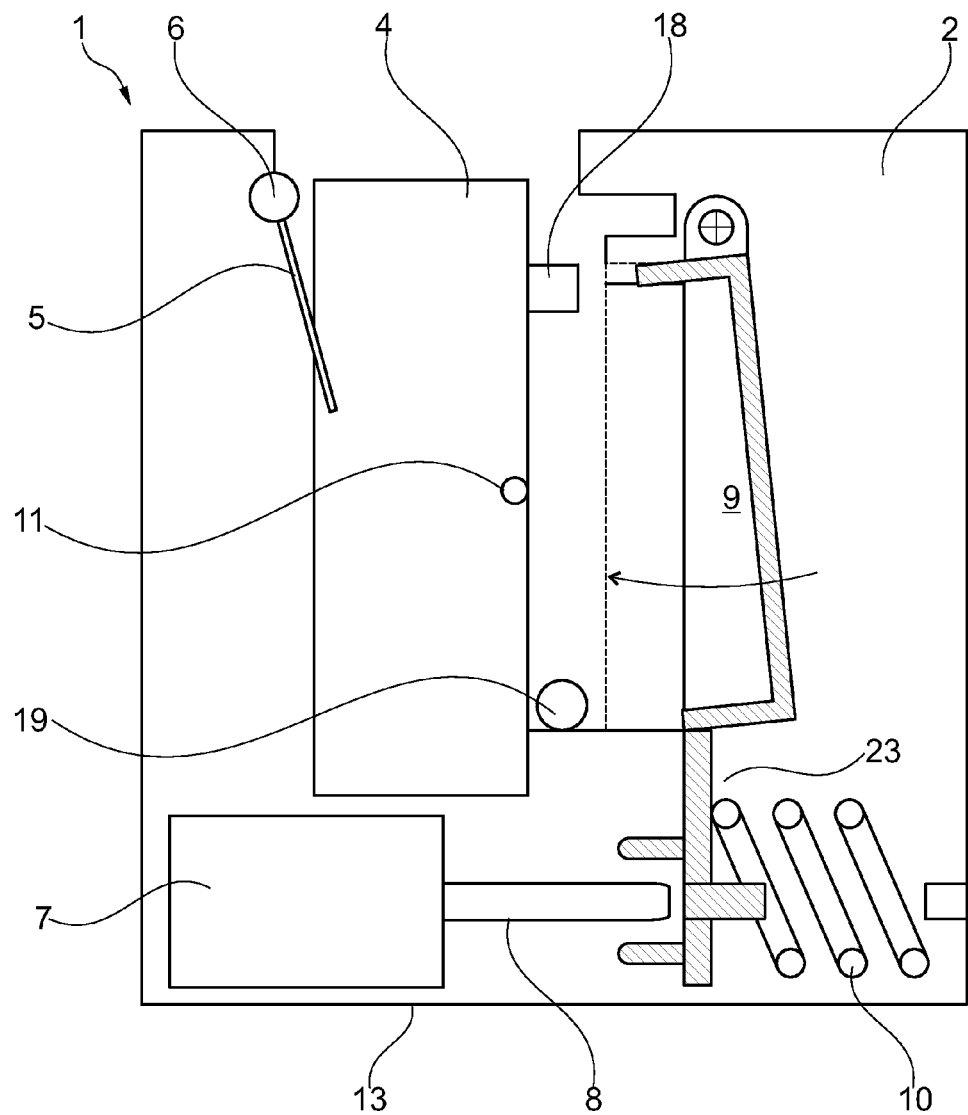
FIG. 6 shows an embodiment of the fragrancing system according to the invention.

In order to prevent the escape of fragrance when the linear actuator 7 is deactivated, according to FIG. 6 one or two seals 18, 19 are disposed on the edge of the fragrance outlet opening from the fragrance storage container 4 on the long side of the fragrance storage container 4 and are positioned at the level of the boundary of the closure mechanism 9. When the opening 11 of the fragrance storage container 4 is closed, the closure mechanism 9 rests on these seals 18, 19, wherein the seals 18, 19 enclose the opening 11 of the fragrance storage container 4.

Figure 7:
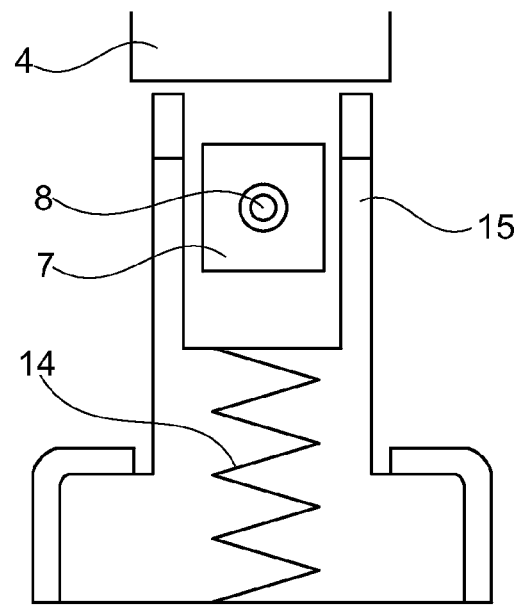
FIG. 7 shows an embodiment of the fragrancing system according to the invention.

FIG. 7 shows a side view of the embodiment of the fragrancing system according to the invention illustrated in FIG. 6, from which it can be seen that the plunger 15, which is pressed by the ejector spring 14 against the fragrance storage container 4, is constructed with two arms and surrounds the linear actuator 7 with the lever 8 without contact, in order to be able to achieve the ejection of the fragrance storage container 4 without problems.

Figure 8:
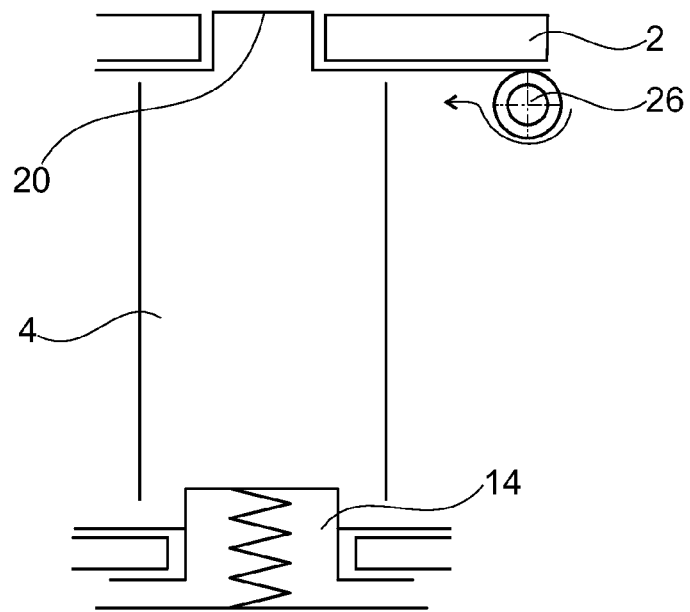
FIG. 8 shows an embodiment of the fragrancing system according to the invention.

A further embodiment of the fragrancing system according to the invention is illustrated in FIG. 8, where the cover 20 of the housing 2 simultaneously forms the closure mechanism for the fragrance storage container 4. Upon the introduction of the fragrance storage container 4 the cover 20 fastened to a spring 26 is pushed to the side. After the fragrance storage container 4 is positioned in the housing interior 3, the spring 26 presses the cover 20 against the seals 18, 19 and thus closes the opening 11 of the fragrance storage container 4. Also in this embodiment the fragrance storage container 4 is pretensioned by an ejector spring 14, which acts from below on the fragrance storage container 4, so that the fragrance storage container 4 can be removed from the housing 2.

Figure 9:
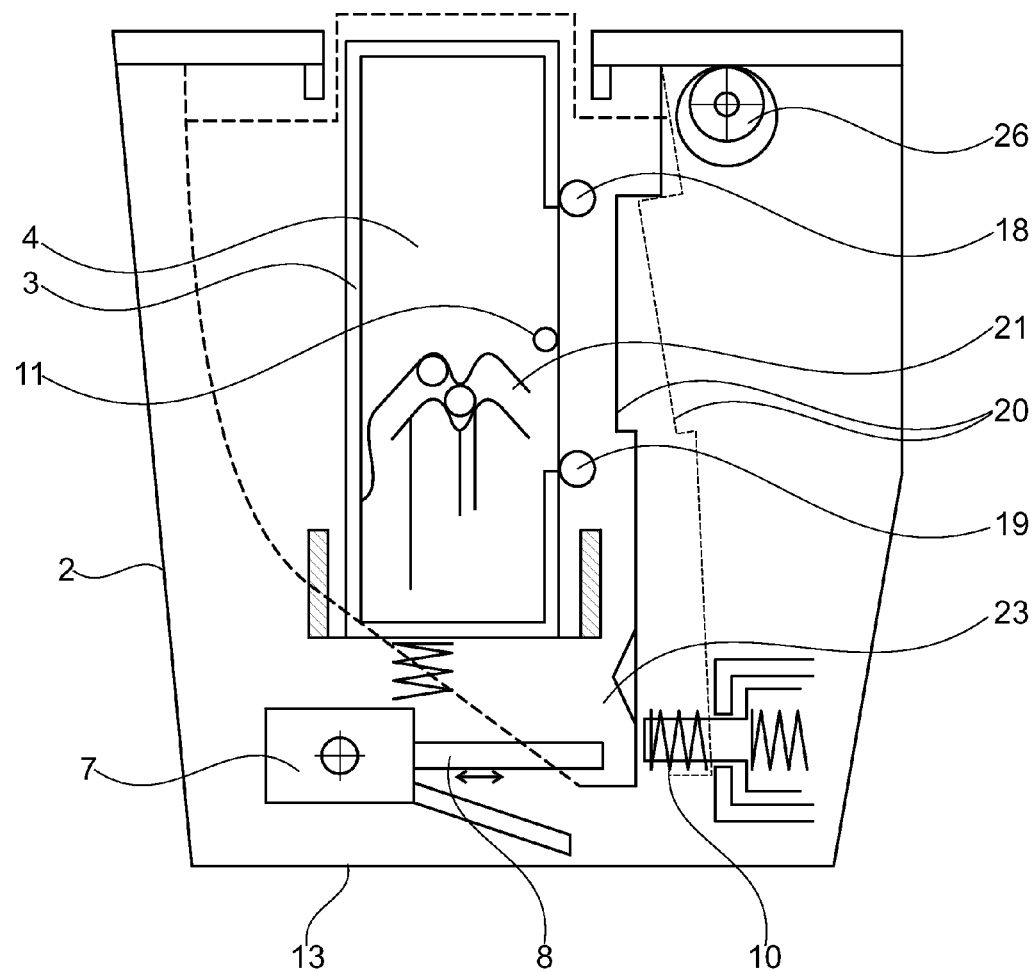
FIG. 9 shows an embodiment of the fragrancing system according to the invention.
Figure 10:
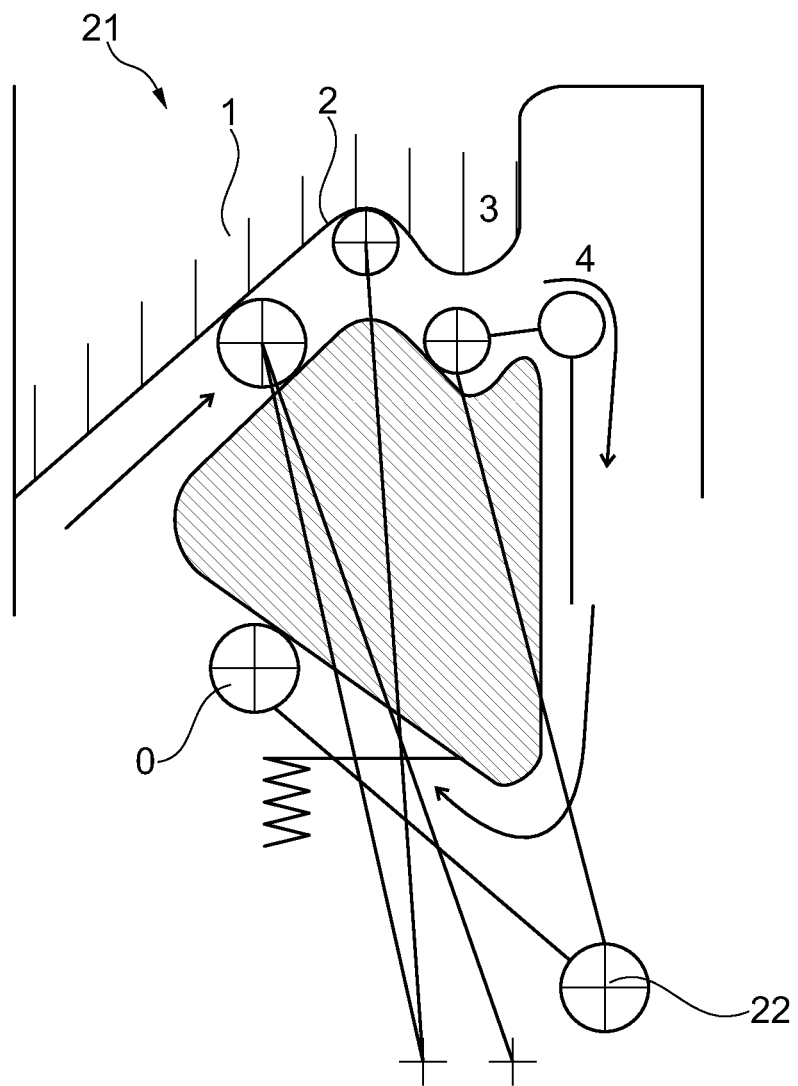
FIG. 10 shows an embodiment of the fragrancing system according to the invention.

A further embodiment of the fragrancing system 1 according to the invention is illustrated in FIG. 9, wherein the fragrance storage container 4 has a push-push mechanism 21 with a cardioid. In this case the push-push mechanism 21 is illustrated in greater detail in FIG. 10 and is released by means of a pin 22 for ejection and for locking of the fragrance storage container 4. In this case the linear actuator 7 is moved axially against the flap overlap 23, wherein the pin 22 engaging in the cardioid formed on the wall of the fragrance storage container 4 adopts different positions. The position 0 represents the starting position. In the position 1 the pin 22 is inserted into the cardioid and deflected within the position 2. In the position 3 the pin 22 is held in the cardioid. In the position 4 the fragrance storage container 4 is freed for dispensing.

Figures 11, 12, 13:
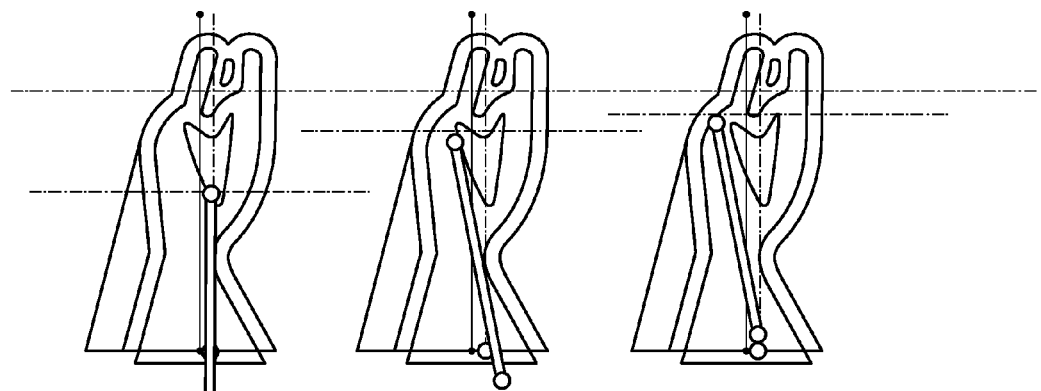
FIG. 11 shows a first state of a push-pull mechanism with a cardioid.
FIG. 12 shows a further state of a push-pull mechanism with a cardioid.
FIG. 13 shows a further state of a push-pull mechanism with a cardioid.
Figures 14, 15, 16:
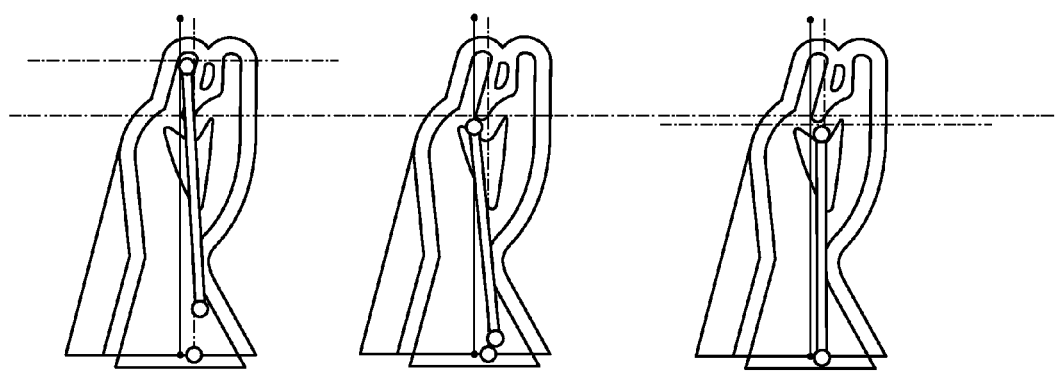
FIG. 14 shows a further state of a push-pull mechanism with a cardioid.
FIG. 15 shows a further state of a push-pull mechanism with a cardioid.
FIG. 16 shows a further state of a push-pull mechanism with a cardioid.
Figures 17, 18, 19:
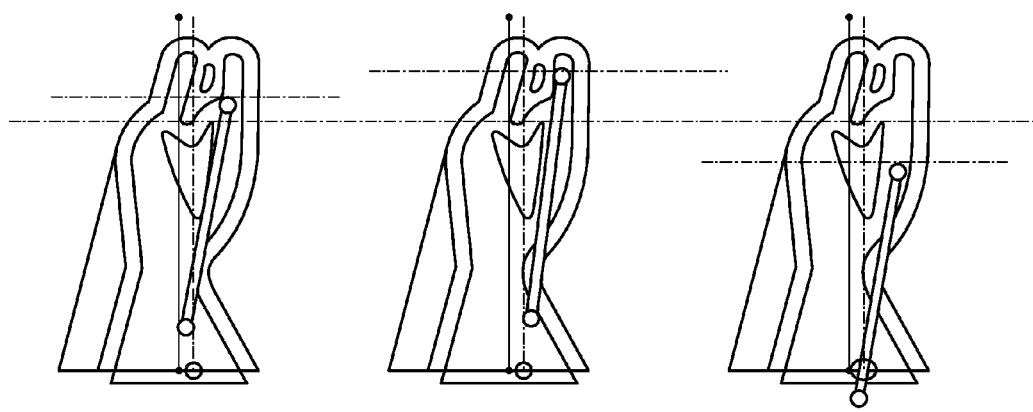
FIG. 17 shows a further state of a push-pull mechanism with a cardioid.
FIG. 18 shows a further state of a push-pull mechanism with a cardioid.
FIG. 19 shows a further state of a push-pull mechanism with a cardioid.

A more precise representation of the positions of the pins 22 is shown in FIGS. 11 to 19. In this case FIGS. 11 to 13 show a first sequence during the insertion of the fragrance storage container 4. In FIGS. 14 to 16 a second sequence of the insertion of the fragrance storage container is made clear, whereas FIGS. 17 to 19 clarify the positions of the pins 22 when the fragrance storage container 4 is pushed out.

Also in this state the position of the cover 20 constructed as a closure mechanism is determined by the linear actuator 7 or the restoring spring 10. In the operational situation in which the linear actuator 7 is disconnected, the fragrance storage container 4 is automatically closed by the cover 20 (FIG. 9).

Figure 20:
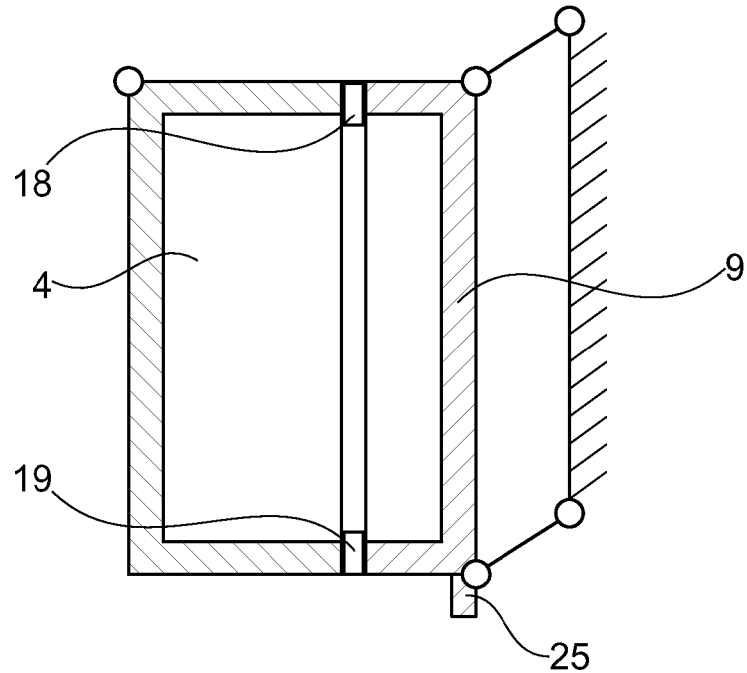
FIG. 20 shows an embodiment of the fragrancing system according to the invention.
Figure 21:
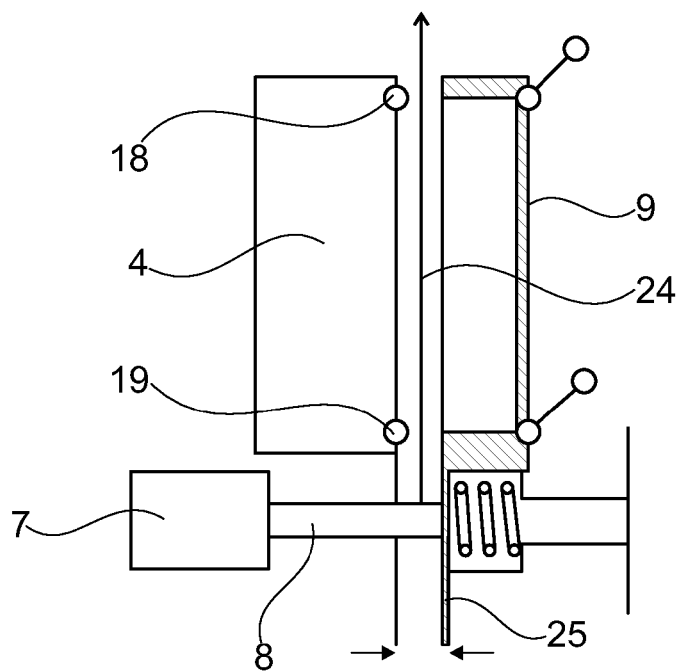
FIG. 21 shows an embodiment of the fragrancing system according to the invention.

In FIG. 20 and FIG. 21 a fragrance storage container 4 is illustrated, wherein by the movement of the linear actuator 7 the closure mechanism 9 is completely pivoted away from the fragrance storage container 4, so that an air channel 24 is freed. FIG. 20 shows the closed state of the fragrance storage container 4, whereas in FIG. 21 the open state is illustrated.

The air channel 24 is connected to a blower, which is not shown in further detail, which moves air for transport of the fragrance released via the opening 11 of the fragrance storage container 4 within the air channel 24 and frees this from the housing 2. In order to ensure a linear movement of the closure mechanism 9, a cover stabilizer 25, which is fastened on the housing 2 and is moved by the linear actuator 7 and the lever 8, acts on the closure mechanism. In this case the blower preferably draws the air in radially from outside. Behind the blower the air channel 24 can divide into two part-channels, wherein the described fragrance storage container 4 is disposed in one part-channel, whereas an ionizer is located in the second part-channel in order to clean the air in the vehicle interior.

The described fragrancing system is mobile and can be placed flexibly in the interior of the motor vehicle, for example in a cup holder or by means of a suction foot at any position in the vehicle interior.

Because of its simple construction it requires only a little installation space and facilitates a quick change of the fragrance storage container 4. The fragrance storage container 4 has at the top a coding for recognition of the fragrance, which is preferably in the form of a color coding or textual display.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A fragrancing system for a motor vehicle, the system comprising:
   a housing in which a replaceable fragrance storage container is insertable, the housing having an opening for dispensing a fragrance that is covered by a closure mechanism that frees the opening for dispensing of the fragrance when actuated by an actuator; and
   a cover for the housing, the cover, which for introduction of the fragrance storage container, is mounted so as to be pivotable about an axis of rotation into a housing interior,
   wherein, when the fragrance storage container is introduced, it is locked by the cover.

2. The fragrancing system according to claim 1, wherein the locking of the fragrance storage container takes place via a projection that is formed on the fragrance storage container or via a notch that is formed on the fragrance storage container and in which the cover pivoted into the housing interior engages.

3. The fragrancing system according to claim 1, wherein an ejector spring pretensioned against the fragrance storage container is arranged below the fragrance storage container on the housing, and wherein, in the event of a movement of the fragrance storage container beyond the lock in a direction of the ejector spring, the cover forming the lock is movable laterally so that the fragrance storage container is led out of the housing.

4. The fragrancing system according to claim 1, wherein the closure mechanism of the opening of the fragrance storage container is formed as a pivotable flap in the housing interior, wherein the flap is rotatably mounted close to an opening in the housing and projects beyond the longitudinal extent of the fragrance storage container and is pivotable out of a rest position closing the opening by a linear actuator disposed below the fragrance storage container and acting on a freely movable flap overlap, and wherein a rotatable bearing and the flap overlap are arranged at opposite ends of the flap.

5. The fragrancing system according to claim 4, wherein the linear actuator is a solenoid or a shape memory actuator.

6. The fragrancing system according to claim 4, wherein a restoring spring, which presses the flap against the opening of the fragrance storage container when the linear actuator is inactive, acts on the side of the flap overlap facing away from the linear actuator.

7. The fragrancing system according to claim 1, wherein an ejection mechanism is constructed as a push-push mechanism with a cardioid.

8. The fragrancing system according to claim 1, wherein the closure mechanism of the opening of the fragrance storage container is formed as a cover of the housing.

9. The fragrancing system according to claim 1, wherein an air ionizer is disposed in the housing in a first part-channel and the fragrance storage container is disposed in a second part-channel.

10. The fragrancing system according to claim 1, wherein a blower for generating a stream of air for transport of the fragrance and/or the ions is arranged below the fragrance storage container and/or below the ionizer.

* * * * *